United States Patent
Huang et al.

[11] Patent Number: 6,083,383
[45] Date of Patent: Jul. 4, 2000

[54] APPARATUS FOR PRODUCTION OF FIBRINOGEN OR FIBRIN GLUE

[76] Inventors: Xun Yang Huang; Gang Liang; Yan Liang, all of 5629 Chestnut Common, Fremont, Calif. 94538

[21] Appl. No.: 09/105,286

[22] Filed: Jun. 25, 1998

Related U.S. Application Data

[60] Provisional application No. 60/051,093, Jun. 27, 1997, abandoned.

[51] Int. Cl.[7] .................................................. B01D 63/00
[52] U.S. Cl. .................. 210/175; 210/321.6; 210/257.2; 210/259; 422/101; 436/177; 530/382
[58] Field of Search ................................ 210/175, 321.6, 210/257.2, 259; 422/101, 288, 269; 604/4, 5, 6; 530/382; 436/177

[56] References Cited

U.S. PATENT DOCUMENTS

| | | | |
|---|---|---|---|
| 4,066,549 | 1/1978 | Oeser et al. | 210/177 |
| 4,627,879 | 12/1986 | Rose et al. | 106/124.1 |
| 4,714,457 | 12/1987 | Alterbaum | 494/37 |
| 5,030,215 | 7/1991 | Morse et al. | 604/410 |
| 5,185,001 | 2/1993 | Galanakis | 604/5 |
| 5,226,877 | 7/1993 | Epstein | 604/35 |
| 5,290,552 | 3/1994 | Sierra et al. | 424/94.64 |
| 5,480,378 | 1/1996 | Weis-Fogh et al. | 604/5 |
| 5,484,396 | 1/1996 | Naficy | 604/4 |
| 5,510,102 | 4/1996 | Cochrum | 424/78.08 |
| 5,520,885 | 5/1996 | Coelho et al. | 422/101 |
| 5,585,007 | 12/1996 | Antanavich et al. | 210/782 |
| 5,587,070 | 12/1996 | Pall et al. | 210/202 |
| 5,643,192 | 7/1997 | Hirsh et al. | 604/4 |
| 5,644,032 | 7/1997 | Lontz | 530/382 |
| 5,738,784 | 4/1998 | Holm et al. | 210/206 |
| 5,750,657 | 5/1998 | Edwardson et al. | 530/382 |

*Primary Examiner*—W. L. Walker
*Assistant Examiner*—Richard W. Ward
*Attorney, Agent, or Firm*—C. P. Chang; Pacific Law Group LLP

[57] ABSTRACT

This invention relates generally to apparatuses and processes for preparing fibrinogen glue from autologous plasma. More particularly, this invention relates to a novel apparatus comprising a plasma membrane separator to extract and separate the autologous plasma from other undesirable compositions in the blood. The autologous plasma is transferred to a membrane separator to provide separation of the fibrinogen from other compositions with a desirable amount of ether or other suitable solvents containing an-OH group in the presence of a mixing means. The fibrinogen so separated is transferred to a fibrinogen collector which is connected to a vacuum pump through a sterile filter to remove the ether or other suitable solvents contained thereof. A freezer is provided to maintain the autologous plasma in the membrane separator and the fibrinogen in the fibrinogen collector at a desirable temperature. Additionally, a constant temperature bisyringe serves to keep the fibrinogen liquid and mixed with thrombin to form a homogeneous clotting to achieve hemostasis and tissue approximation. A second embodiment which provides a method of producing fibrin glue without the need of ether or organic solvents is also disclosed.

2 Claims, 4 Drawing Sheets

APPARATUS FOR PRODUCTION OF FIBRINOGEN OR FIBRIN GLUE

This application is based on a provisional application Ser. No. 60/051,093 filed Jun. 27, 1997, now abandoned.

FIELD OF THE INVENTION

This invention relates generally to processes and apparatuses employed for preparing fibrinogen from autologous plasma. More particularly, this invention relates to a novel apparatus employed to produce fibrin glue from autologous plasma by applying a novel preparation process whereby such preparation is carried out in a completely insulated and sterile system for preventing the preparation from being contaminated due to exposure to the air. Additionally, it relates to a constant temperature bisyringe serving to keep the fibrin glue liquid and being mixed with thrombin to form a homogeneous clotting to achieve hemostasis and tissue approximation.

BACKGROUND OF THE INVENTION

Although fibrin glue is more commonly used to repair wounds in surgical procedures and other clinical treatments, the effective application of the fibrin glue is still hindered by several difficulties. Specifically, the production of a high concentration fibrin glue generally requires long hours of processing. Such time consuming processes limit the practical application and utility of such production cycles in an urgent application. Some production processes are also limited by the fact that chemical agents will cause fibrin glue protein to denature. Furthermore, in some production processes, the plasma is exposed to air and environments where viruses or bacteria may enter into the plasma mixtures and cause contamination. Incompatible blood may also cause immunological reactions. These risks further limit the practical usefulness and the safety of such applications when the fibrin glue is employed as a wound sealant.

Fibrin glue produced from basic physiological functions is becoming more popular for application to a variety of surgical procedures. A stable fibrin clot is produced when the fibrinogen, thrombin and factor XIII are activated in the presence of calcium ions. The application of the fibrin glue to the wound sites allows the restoration of the structural properties of the wounds by the glue. Furthermore, the fibrin glue contains components that can stimulate the repairing, or healing of the wounds.

In U.S. Pat. No. 4,627,879, entitled "Fibrin Adhesive Prepared As A Concentrate From Single Donor Fresh Frozen Plasma", Rose et al. discloses a method of preparing a cryo-precipitated suspension containing fibrinogen and factor XIII useful as a precursor in the preparation of a fibrin glue. The method includes the steps of (a) freezing fresh frozen plasma from a single donor, such as a human or other animal, at −80° C. for at least six to twelve hours; (b) raising the temperature of the frozen plasma to about room temperature so as to form a supernatant and cryo-precipitated suspension containing fibrinogen and factor XIII; and (c) recovering the cryo-precipitated suspension. The cryo-precipitated suspension may be useful as a precursor for preparing the fibrin glue. However, the Rose et al. invention does not provide an effective method to produce a fibrin glue in a sufficient concentration and with strong adhesion properties for clinical and surgical applications. In addition, the long, time-consuming process of [preparing the] fibrin glue preparation also limits its practical usefulness.

In U.S. Pat. No. 5,185,001, entitled "Method of Preparing Autologous Plasma Fibrin and Application Apparatus Therefor" issued on Feb. 9, 1993), Galanakis discloses a method of preparing autologous plasma fibrin perioperatively to induce local hemostasis wherein the autologous plasma fibrin is simultaneously expelled onto a treatment site along with a physiologically acceptable thrombin solution to effect hemostasis at the site. Galanakis also discloses an apparatus for simultaneously expelling the contents of vessels which separately contain the autologous plasma fibrin and thrombin solution. Further disclosed in the Galanakis patent are a kit for obtaining a sample of blood, extracting plasma fibrin therefrom, as well as all necessary syringes, needles and reagents. The apparatus and method for preparing the autologous plasma fibrin disclosed in the Galanakis patent is a low concentration plasma fibrin which is suitable for inducing local hemostasis which may be useful for smaller wounds. However, the plasma fibrin added with the thrombin solution would not provide a total solution for surgical applications where larger wounds are usually involved.

In U.S. Pat. No. 5,226,877, entitled "Method and Apparatus for Preparing Fibrinogen Adhesive From Whole Blood" (issued on Jul. 13, 1993), Epstein discloses a process and an apparatus for one-step preparation of a fibrinogen adhesive by polyethylene glycol-mediated precipitation from plasma. The methods and apparatus permit preparation of an autologous fibrinogen adhesive composition from the patient during surgery and can be applied generally to provide such compositions. Also disclosed in the Epstein invention are an apparatus and method for application of a sealant comprised of the fibrinogen adhesive composition. According to Epstein, after the plasma is separated from the red blood cells, it is treated directly at the ambient temperature without prior treatment to remove thrombin, with a physiologically acceptable nontoxic precipitant. A preferred precipitant is a nontoxic polymer, e.g. polyvinyl alcohol and polyethylene glycol (PEG). The precipitant is supplied as concentrated solution to mix with plasma to yield a concentration effective in precipitating the adhesive composition.

The Epstein method is useful in producing the fibrinogen adhesives; however it has a problem wherein the precipitant, including the nontoxic polymers, may cause unknown side effects when added to the blood plasma, as these precipitants are not removed from the adhesive and are applied directly to the blood of a patient. Additives which are not removed are causes for concern in that unknown, harmful agents may be introduced, and may not be easily discoverable until many years later. The Epstein method also produces albumin precipitants and other complex proteins that will influence the fibrin glue's adhesive and hemostatic effects.

In U.S. Pat. No. 5,290,552, entitled "Surgical Adhesive Material" (issued Mar. 1, 1994), Sierra et al. disclose a surgical adhesive which is comprised, in an aqueous composition, of fibrinogen, FXIII, collagen, thrombin, $Ca^{++}$ and an optionally antifibrinolytic agent. In order to extract the fibrinogen, which constitutes the adhesive component from the patient's own plasma, the plasma cryo-precipitate is prepared by freezing the plasma to −20° C. and then slowly thawed overnight. The thawed plasma is then centrifuged to harvest the plasma precipitate. This process is disadvantageous in that extra long hours are required to produce the surgical adhesive through the low temperature process. Although the fibrinogen components are produced in a closed system, higher risks may be involved during the preparation process due to the possible contamination of the fibrinogen adhesive through contact with air and the possibility of undesirable immunological response due to the addition of collagen.

In U.S. Pat. No. 5,510,102, entitled "Plasma and Polymer Containing Surgical Hemostatic Adhesive" (issued on Apr. 23, 1996), Cochrum discloses an autologous platelet-rich plasma and a bio-compatible polymer containing hemostatic adhesive agents. The agents have strong hemostatic properties when applied to a bleeding wound or vessel. Although the platelet-rich plasma may be produced from the method disclosed in the Cochrum patented invention, risks of unknown side effects to the human body may still be a concern due to the addition of the bio-compatible polymer into the plasma. This is especially true when the mixture is to be applied directly to the vessel wounds wherein such plasma will be absorbed and carried throughout the body via blood vessels. Such risks may preclude the Cochrum plasma from being used in surgical or clinical applications.

In U.S. Pat. No. 5,520,885, entitled "Fibrinogen Processing Apparatus Method and Container", Coelho et al. disclose an instrumentality for promulgating the cryo-precipitation of fibrinogen from a blood product. The method, apparatus and container are disclosed in this patented invention; however, as discussed above, when a cryo-precipitation method is employed, long hours of freezing and thawing are required, which renders the application of such methods and apparatus to practical surgical or clinical environments ineffective.

Therefore, a need still exists in the art of fibrin glue production to provide a novel and effective process such that the production of the fibrin glue adhesive can be accomplished in less time. Furthermore, the fibrinogen adhesive produced must be free of contamination and additives such that application of the fibrin glue to the human body in surgical and clinical treatments can be safely administered.

SUMMARY OF THE INVENTION

For the foregoing reasons, it is an objective of the present invention to provide new, simple and convenient techniques to produce fibrin glue, with less preparation time, and to enable those of ordinary skill in the art to overcome the aforementioned difficulties and limitations encountered in the prior art.

Specifically, it is an object of the present invention to provide new techniques and an apparatus to produce fibrin glue employing autologous plasma wherein ether is used as a removable precipitant and the fibrin glue is obtained from the autologous plasma. This fibrin glue can be prepared in a few hours, and can be practically and safely applied.

One other object of the invention is to provide new techniques and apparatus to produce fibrin glue employing autologous plasma wherein the preparation of the fibrin glue is performed in a closed and sterile system; as such, the concern of infectious diseases resulting from blood contamination such as the AIDS or hepatitis viruses, as is possible in an open system, may be minimized or alleviated.

Another object of the present invention is to provide new techniques and apparatus to produce fibrin glue employing autologous plasma wherein ether is used as a removable precipitant. The ether employed in the present invention can be completely removed by evaporation within a sterile system. As with the ether, the precipitant can also be completely removed. As such, the concern of the side effects resulting from protein denaturation caused by chemical or bio-compatible additives in the fibrin glue, as is present in prior art, may be eliminated.

Another object of the present invention is to provide new techniques and apparatus to produce fibrin glue employing autologous plasma wherein ether is used as a removable precipitant to produce fibrin glue with a high tensile strength resulting from a high concentration of fibrinogen. Such fibrin glue is also conducive to practical application as it may be refrigerated and stored at 0° C. for up to two months, while maintaining its quality characteristics.

Another object of the present invention is to provide new techniques and apparatus to produce fibrin glue employing autologous plasma in a simplified process: 20 minutes of freezing at −20° to −80° C. and 20 minutes of thawing at 00, repeated 8–10 times and operated in conjunction with an apparatus according to the invention.

Another object of the present invention is to provide a new constant temperature (0°–37° C.) syringe for mixing fibrin glue, thrombin and Ca++ to form a homogeneous clotting agent for increased treatment effect.

Another object of the present invention is to provide a new antithrombotic agent-Tetradrine and T-B membrane (Fibrin glue-Tetrandrine membrane) for dissolving thrombosis and preventing thrombosis formation during interventional operation.

These and other objects and advantages of the present invention will no doubt become obvious to those of ordinary skill in the art after having read the following detailed description of the preferred embodiment which is illustrated in the various drawing figures.

DETAILED DESCRIPTION OF THE PREFERRED EMBODIMENT

Figure 1:
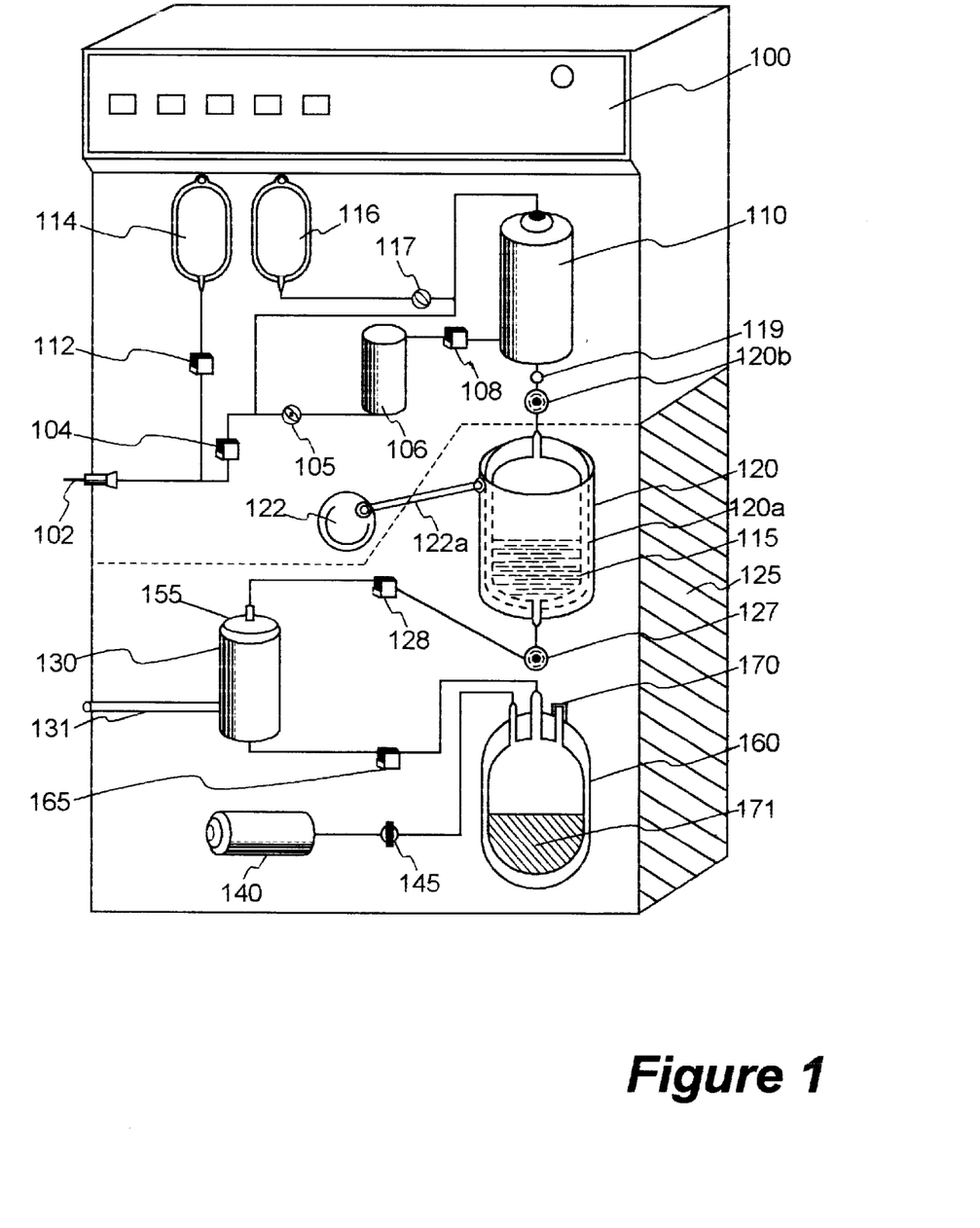
FIG. 1 is a perspective view illustrating an embodiment of the apparatus according to the present invention.

Referring to FIG. 1, there is shown an apparatus 100 employed for producing the fibrinogen of high concentration and high tensile strength according to the techniques of this invention. The blood drawn from a patient is first received from a needle 102. The blood is immediately mixed with an anticoagulant drawn from a plasma bag 114, which serves as a reservoir for the anticoagulant, through the action of a peristaltic pump 112. The patient's blood is then pumped by a blood pump 104 to a re-infusion reservoir 106 which is then transferred by a concentrated cell pump 108 to a plasma membrane separation device 110 where an autophoresis process is carried out to extract the plasma from the patient's blood. As a result of such autophoresis process, a portion of the patient's blood which consists mostly of red blood cells is transferred to a second plasma bag 116 for subsequent re-infusion back to the patient during a surgical procedure. The plasma membrane separation device 110 can be either a membrane or a centrifuge.

The plasma extracted by the plasma membrane separation device 110 is transferred by applying the concentrated cell pump 108 through a transfer line 101 to a third plasma bag or a plastic cup 120a held within a plasma container 120. A red cell and hemoglobin detector 119 is placed on the transfer line 101 between the plasma membrane separation device 110 and the third plasma bag or the plastic cup 120a to monitor the red cell and the hemoglobin counts of the plasma entering into the third plasma bag or the plastic cup 120a. A desirable amount of ether or other suitable [R—OH] solvents containing an-OH group as well as anticoagulants may be introduced into the third plasma bag or the plastic cup 120a through an openable inlet 120b typically used in a plasma bag for delivering or withdrawing substances from the plasma without compromising its sterile condition. The plasma container 120 is connected to a rotary disk 122 through a connecting rod 122a. The plasma is thoroughly mixed with ether and the anticoagulant by shaking the container 120 for four to five minutes by employing the rotary disk 122. The plasma container 120 is placed in a freezer 125 where the temperature is controlled at zero degrees Celsius, i.e., 0° C. In a preferred embodiment, the amount of plasma is approximately 250–300 cc containing about 8% of ether therein. The mixture also contains about 3.6–4.5% of anticoagulant therein, which includes sodium citrate and sterile water. After shaking and thorough mixing, the temperature of the freezer is adjusted to about –20° C. The temperature of the container 120 with the plasma mixture contained therein is maintained at that temperature for about two to three hours. The temperature of the freezer is then readjusted to about 0° C.

The plasma mixture is then transferred by a first fibrin glue pump 128 from the third plasma bag 120a through a tube 126 and a fibrin glue clamp 127 to a fibrin glue membrane separation device. The fibrin glue membrane separation device can be a filter device, a membrane or, preferably, a centrifugal device to provide centrifugal separation of the fibrin glue from other compositions in the plasma. The centrifugal device comprises a rotational cylindrical container 155 which includes a plurality of membrane layers. The centrifugation is provided to rotate with a rotational speed ranging from 300 to 4000 revolutions per minute (RPM). Under such a centrifugal separation process, the supernatant of the plasma mixture is separated from fibrinogen wherein the supernatant fibrinogen is collected at the bottom of the cylindrical container 155. The fibrinogen is then transferred by a second fibrin glue pump 165 via a tube to a fibrinogen collector 160 and syringe 170, and ready for surgical or other therapeutic applications. A vacuum pump 140 is connected to the fibrinogen collector 160 through a sterile filter 145 to remove the ether contained in the fibrinogen collector 160 immediately after such fibrin glue is transferred to the fibrinogen collector 160.

It should be noted that the aforementioned apparatus and process can be significantly simplified by combining the shaking and the centrifugal process together as one single unit. Referring still to FIG. 1, as a preferred embodiment (not shown), the third plasma bag 120a and its holding container, the plasma container 120 can be eliminated by replacing them with the rotational cylindrical container 155. As such, the plasma extracted by the plasma membrane separation device 110 is transferred by applying the concentrated cell pump 108 through a transfer line 101 to the rotational cylindrical container 155 which then provides simultaneously a rotational speed as is provided by the centrifugal device and a shaking motion as is provided by the rotary disk 122 to the plasma mixture so that the plasma mixing and separation process can be performed simultaneously. In addition, the vacuum pump 140 can be connected directly to the rotational cylindrical container 155, rather to the fibrinogen collector 160, through the sterile filter 145 to remove the ether contained in the plasma mixture during the centrifugal separation operation. It is therefore apparent that the simplified procedure described herein eliminates the needs for the rotary disk 122, the connecting rod 122a, the third plasma bag 120a, the plasma container 120 and at least one pump without compromising its functions and efficiency for producing fibrinogen from a patient's own blood. It should be further noted that, for the purposes of convenience, all of the pumps (except for the vacuum pump) described in the invention are designated by their respective functions. However, it is highly desirable that these pumps are peristaltic pumps to transfer the blood and plasma within a closed and sterile system as is required by the invention.

Figure 2:
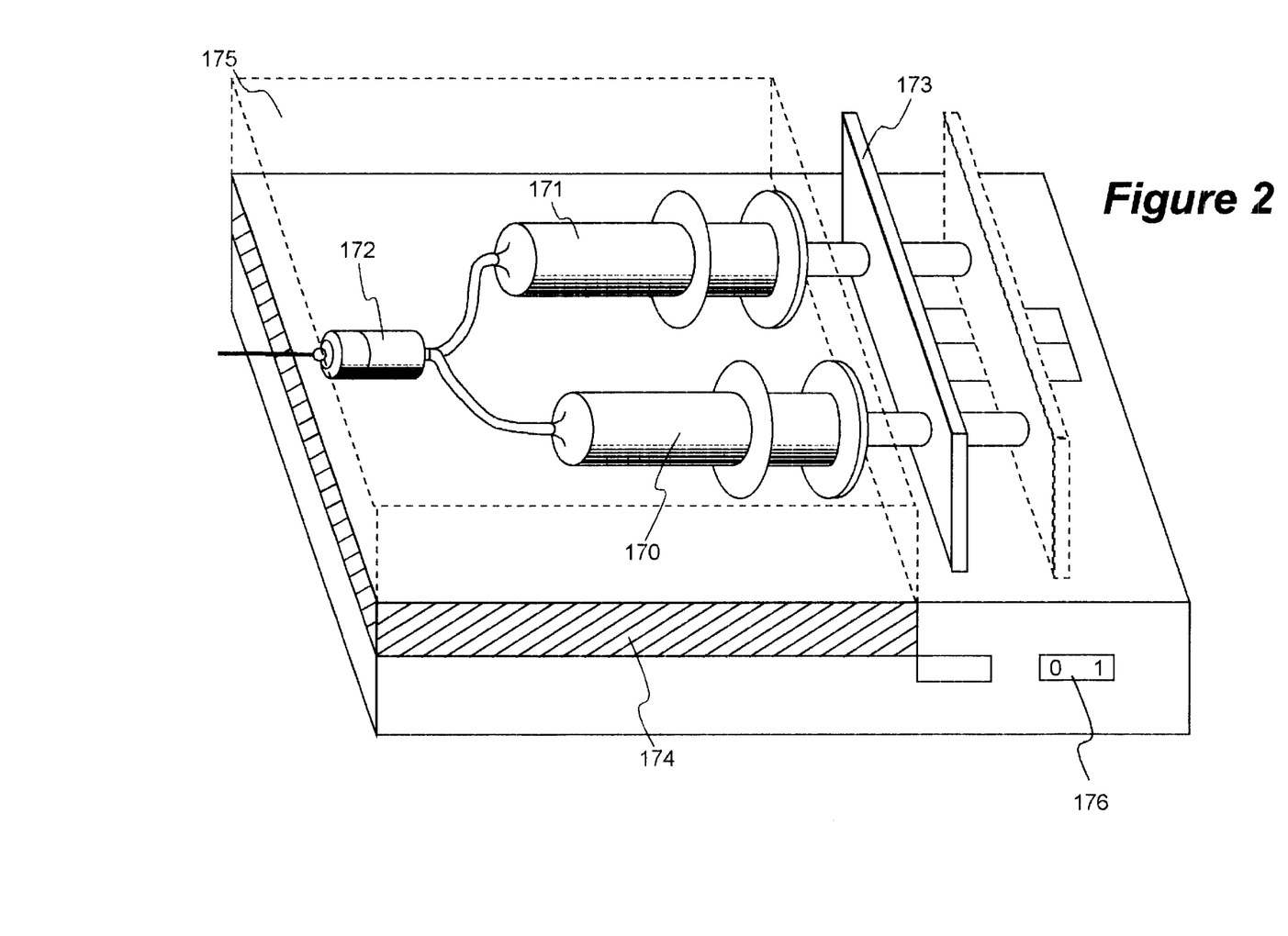
FIG. 2 is a perspective view illustrating a constant temperature bisyringe mixer according to the present invention.

Referring to FIG. 2, there is shown a constant temperature bisyringe mixer provided by the invention. As described above, once the fibrinogen is transferred to fibrinogen collector 160 and syringe 170, it is ready for surgical or other therapeutic applications. However, since fibrin glue is known to exist physically as a semi-solid material at room temperature, its such surgical or other therapeutic applications may be severely hampered if the fibrin glue is prematurely solidified before it can be adequately mixed with thrombin or applied to a wound. To address this problem, a constant temperature bisyringe mixer is provided herein by the invention. As shown in FIG. 2, the syringe 170, which contains fibrin glue, is mounted parallel along with a second syringe 171 to an autopropeller 173. The second syringe contains thrombin and Ca++. One end of each of the syringes 170 and 171 is connected to a mixer 172. When the autopropeller is turn on through the activation of a power switch 176, it produces a desirable downward force equally to the syringe 170 and Syringe 171 at same time, which pushes out the fibrin glue and thrombin and Ca++ from both of the syringes into the mixer 172 at which the fibrin glue and thrombin and Ca++ is mixed to form a homogeneous mixture. The syringe 170 and the syringe 171 are installed within a temperature control device 174 and is covered and protected by a thermal insulation cover 175 to ensure that a constant temperature of 37° C. is achievable for the syringes. Since fibrin glue is known to exist physically in a liquid form at 37° C., it can be easily mixed with thrombin and Ca++ to produce a homogeneous fibrin glue with sufficient tensile strength suitable and more convenient for surgical or other therapeutic applications.

Figure 3:
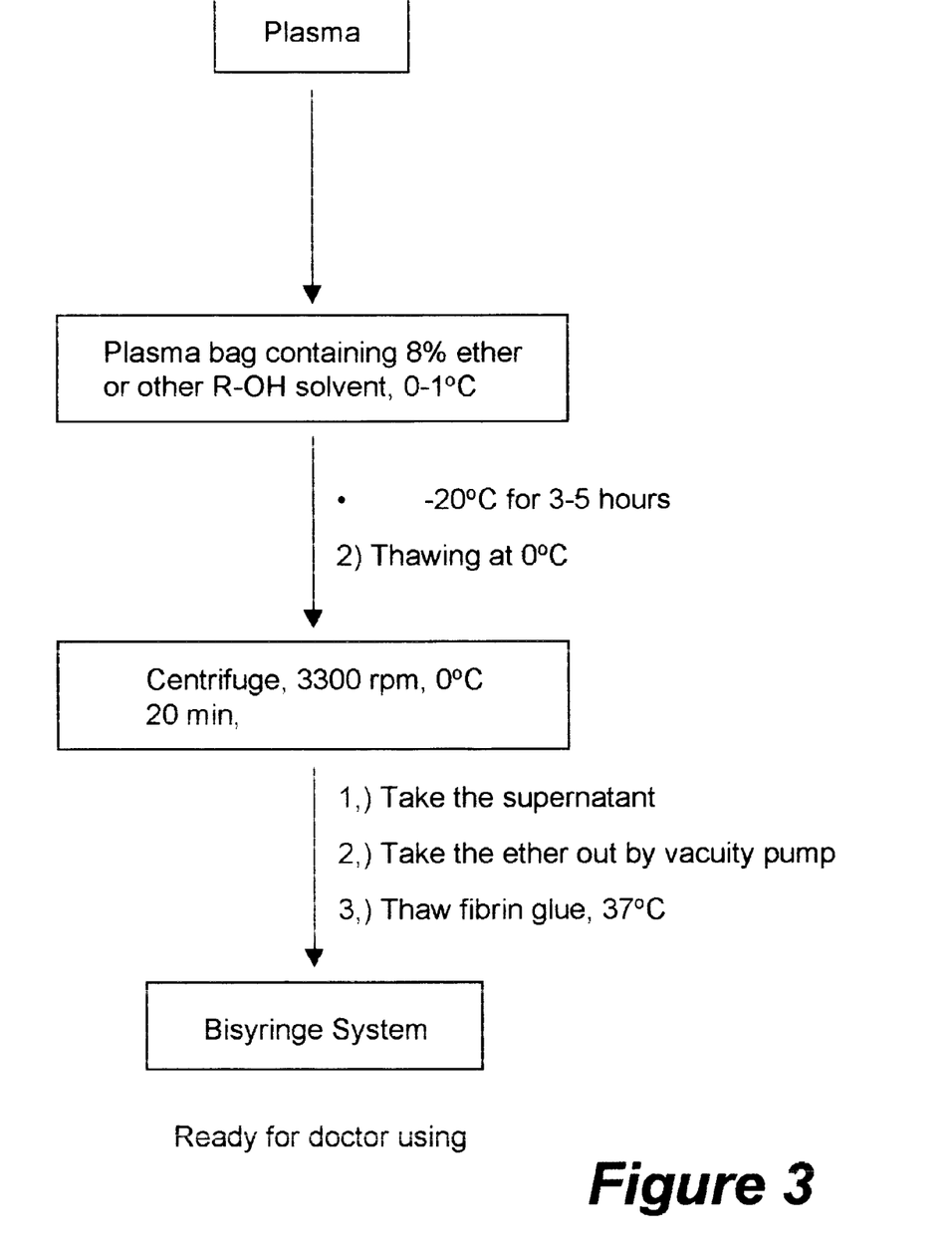
FIG. 3 is a schematical illustration of producing fibrin glue by ether extraction according to the present invention.

In one specific example in producing the fibrin glue as is schematically illustrated in FIG. 3, blood plasma extracted from a patient is mixed with 3.6–3.8% sodium citrate and sterile water in the plasma container 120 having a total volume of about 300 cc which is mixed with 12.6 cc of ether at a temperature of about 0° C. The mixture is then shaken for ten minutes. The mixed plasma is then frozen at –20° C. for about three hours. The temperature of the plasma mixture is then adjusted to 0° C. and processed by the centrifugal process rotated at 3300 RPM for about 20 minutes or filtered through a membrane for separation of the supernatant and the fibrin glue. In the meantime, the ether is removed by operating the vacuum pump 140 during the centrifugal operation. The fibrin glue is then warmed to a temperature of about 37° C. and ready for application to heal the wounds of a patient. In this actual fibrin glue production process, the entire procedure takes no more than four to five hours. As shown in Table 1 below, the above described apparatus and procedures are repetitively applied for producing the fibrin glue, with yields ranging from 70% to 95%, with an average yield of about 82%, and a fibrinogen concentration above 6200 mg/dl which has a tensile strength of at least 400 kg/cm as measured against a pig skin tensile strength test.

TABLE 1

Fibrinogen concentration and yield employing ether extraction according to the invention

| Date | No. | Plasma (cc). | Fibrinogen of Plasma (mg/dl) | Fibrinogen of Fibrin Glue (mg/dl) | Fibrin Glue (cc.) | Yield (%) |
|---|---|---|---|---|---|---|
| 3-10-97 | 1 | 127 | 232 | 6021 | 3.6 | 73 |
| 3-11-97 | 2 | 128 | 232 | 5124 | 3.5 | 69.9 |
| 3-14-97 | 3 | 141 | 208 | 6230 | 3.6 | 76 |
| 3-15-97 | 4 | 114 | 208 | 6121 | 3.4 | 87 |
| 3-16-97 | 5 | 293 | 198 | 6400 | 8.8 | 96 |
| 3-18-97 | 6 | 311 | 152 | 6550 | 6.5 | 89 |

Figure 4:
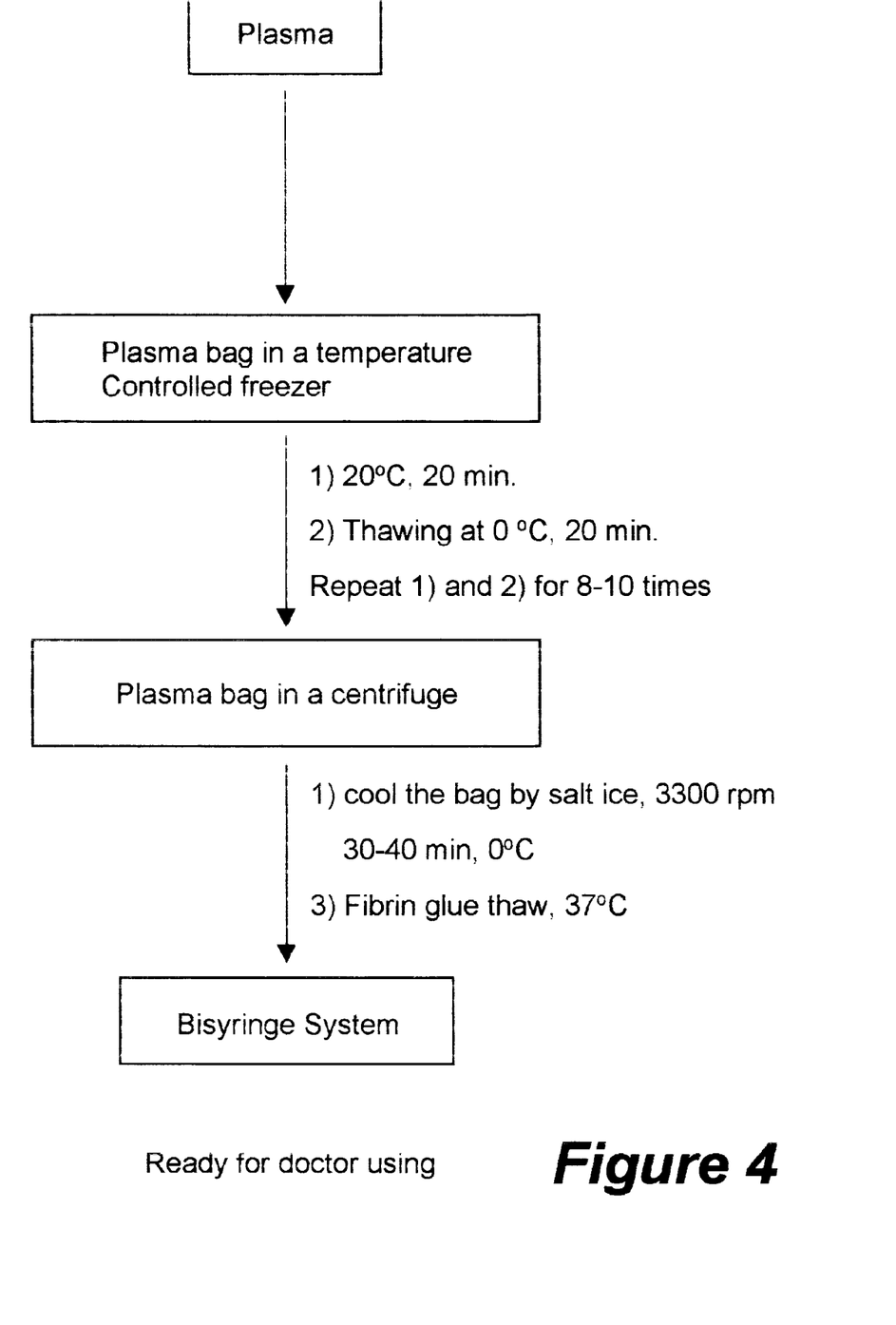
FIG. 4 is a schematical illustration of producing fibrin glue without ether extraction according to the present invention.

In another specific example in producing the fibrin glue according to the invention as is schematically illustrated in FIGS. 4 and 1, blood plasma extracted from a patient is not mixed with any amount of ether or other R—OH solvents. Instead, after the blood plasma is mixed with 3.6–3.8% sodium citrate and sterile water in the third plasma bag or the plastic cup 120a of the plasma container 120, the blood plasma is kept in the temperature controlled freezer 125 at −20° C. to −80° C. for 20 minutes. The temperature is then adjusted to 0° C. for 20 minutes. This cycle of freeze and thaw is repeated for 8–10 times followed by transferring the plasma to the rotational cylindrical container 155, which is controlled by the temperature controlled freezer at 37° C. to thaw the fibrin glue. The syringe 171 is then used to remove and collect the fibrin glue. Since this process eliminates the need for ether or other R—OH solvents, the vacuum pump 140 and the sterile filter 145 can be further eliminated from the apparatus to achieve additional simplification of the apparatus according to the invention. In addition, the whole process is conducted in a closed operation system pursuant to FDA standards employing the patient's own plasma, thereby avoiding any kind of infectious disease. The above process takes only 5–7 hours to prepare the fibrin glue, with a concentration of 6000 mg/dl–8000 mg/dl. The yield of fibrinogen according to this method is above 80%.

In still another specific example, the preparation of anti-thrombotic membranae employing the fibrin glue coated with tetrandrin for medical applications such as forming a antithrombotic membranae on the catheter stent is also provided by the invention. Specifically, the catheter stent is immersed in a series of test tubes, each for 2–3 minutes as follows: (1) test tube #1 for 3–4 c.c. eggs white protein; (2) test tube #2 for 3–4 c.c. fibrin glue; (3) test tube #3 for 3–4 c.c. thrombin and Ca++; (4) test tube #4 for 3–4 c.c. sterile water; (5) test tube #5 for 3–4 c.c. sterile water; and (6) test tube #6 for 3–4 c.c. tetrandrine or other antithrombotic agent. It is noted that the orders described above can be changed according to situation. The antithrombotic activities of the antithrombotic membrane according to the invention are illustrated in the data shown in Tables 2, 3, 4, 5 and 6 below.

TABLE 2

The antithrombotic activities of tetrandrine as expressed as dissolving clotting formed by fibrinogen and thrombin

| No | Plasma | 0.9% saline | tetrandrine | Thrombin | Clotting |
|---|---|---|---|---|---|
| Control | 0.4 c.c. | 0.2 c.c. | no | 100 ul | Clotting (immediately) |
| Treatment | 0.4 c.c. | 0.2 c.c. | 1.2 mg/ml | 100 ul | no clotting |

TABLE 3

The antithrombotic actives of antithrombotic membrane Coated with tetrandrine for dissolving the clotting of fibrinogen and thrombin

| No | Plasma c.c. | tetrandrine ul (1.2 mg/ml) | time minutes | thrombin ul | time minutes | fibrinogen mg/dl | P Value |
|---|---|---|---|---|---|---|---|
| 1 | 0.5 | 200 | 20 | 100 | 20 | 490 | |
| 2 | 0.5 | 200 | 20 | 100 | 20 | 281 | |
| 3 | 0.5 | 200 | 20 | 100 | 20 | 343 | |
| 4 | 0.5 | 200 | 20 | 100 | 20 | 306 | |
| 5 | 0.5 | 200 | 20 | 100 | 20 | 693 | |
| 6 | 0.5 | 200 | 20 | 100 | 20 | 257 | |
| 7 | 0.5 | 200 | 20 | 100 | 20 | 220 | |
| 8 | 0.5 | 200 | 20 | 100 | 20 | 281 | |
| 9 | 0.5 | 200 | 20 | 100 | 20 | 294 | |
| 10 | 0.5 | 200 | 20 | 100 | 20 | 514 | |
| 11 | 0.5 | 200 | 20 | 100 | 20 | 502 | |
| 12 | 0.5 | 200 | 20 | 100 | 20 | 514 | |
| 13 | 0.5 | 200 | 20 | 100 | 20 | 355 | |
| 14 | 0.5 | 200 | 20 | 100 | 20 | 85 | |
| P < 0.05 | | | | | | | |
| Control 1 | 0.5 | | 20 | 100 | 20 | 539 | |
| Control 2 | 0.5 | | 20 | 100 | 20 | 416 | |
| Control 3 | 0.5 | | 20 | 100 | 20 | 747 | |
| Control 4 | 0.5 | | 20 | 100 | 20 | 772 | |
| Control 5 | 0.5 | | 20 | 100 | 20 | 539 | |
| Control 6 | 0.5 | | 20 | 100 | 20 | 113 | |
| Control 7 | 0.5 | | 20 | 100 | 20 | 306 | |
| Control 8 | 0.5 | | 20 | 100 | 20 | 612 | |
| Control 9 | 0.5 | | 20 | 100 | 20 | 980 | |
| Control 10 | 0.5 | | 20 | 100 | 20 | 502 | |
| Control 11 | 0.5 | | 20 | 100 | 20 | 477 | |
| Control 12 | 0.5 | | 20 | 100 | 20 | 710. | |
| Control 13 | 0.5 | | 20 | 100 | 20 | 1225 | |
| Control 14 | 0.5 | | 20 | 100 | 20 | 845 | |

TABLE 4

Inhibition of clotting of CaCl$_2$ and plasma by tetrandrine

| No. | plasma (c.c.) | saline (c.c.) | thrombin (ul) | CaCl$_2$ (c.c.) | tetrandrine (c.c.) | clotting |
|---|---|---|---|---|---|---|
| 1 | 0.4 | 1 | 100 | 0 | 0 | clotting immediately |
| 2 | 0.4 | 0 | 0 | 0.2 | 0 | clotting |
| 3 | 0.4 | 0 | 100 | 0.2 | 0.2 | no clotting |
| 4 | 0.4 | 0 | 0 | 0.2 | 0.2 | no clotting |

TABLE 5

Inhibition of clotting platelet and thrombin by tetrandrine

| No. | platelet | thrombin | tetrandrine | saline | clotting time |
|---|---|---|---|---|---|
| 1 | 0.1 c.c. | 100 ul | 0 | 0 | clotting immediately |
| 2 | 0.1 c.c. | 100 ul | 100 ul | 0 | no clotting |
| 3 | 0.1 c.c. | 100 ul | 0 | 100 ul | clotting immediately |

TABLE 6

Correlation of the clotting time of fibrinogen and thrombin to the concentrations of tetrandrine

| No. | Plasma (cc) | Tetrandrine (ul) | Saline | Thrombin (ul) | Delayed in Clotting Time (min) |
|---|---|---|---|---|---|
| 1 | 0.5 | 10 | 0 | 100 | 2 |
| 2 | 0.5 | 20 | 0 | 100 | 5 |
| 3 | 0.5 | 30 | 0 | 100 | 5 |
| 4 | 0.5 | 40 | 0 | 100 | 5 |
| 5 | 0.5 | 50 | 0 | 100 | 5 |
| 6 | 0.5 | 60 | 0 | 100 | 10 |
| 7 | 0.5 | 70 | 0 | 100 | 10 |
| 8 | 0.5 | 80 | 0 | 100 | 10 |
| 9 | 0.5 | 90 | 0 | 100 | 10 |
| 10 | 0.5 | 100 | 0 | 100 | 10 |
| 11 | 0.5 | 150 | 0 | 100 | No clotting (complete inhibition) |
| Control | | | | | clotting immediately |

As shown in the foregoing data, the antithrombotic activities of the antithrombotic membrane prepared according to the invention is suitable for treatment of the thrombosis or for preventing the thrombosis recurrent in a patient's blood vessel.

Therefore, the present fibrin glue invention provides new techniques which require less preparation time and employs simple and convenient processes, thereby enabling those of ordinary skill in the art to overcome the difficulties and limitations encountered in the prior art. Specifically, the new techniques and apparatus disclosed herein uses ether as a removable precipitant, and whereby the fibrin glue is obtained by applying six to eight twenty-minutes-freezing-then-twenty-minutes-thawing cycles to the plasma, ensuring that the fibrin glue can be prepared in a matter of a few hours, and the production cycles can be practically and safely applied. Furthermore, the preparation of the fibrin glue is performed in a closed and sterile system whereby the concern of blood contamination due to exposure to air can be eliminated. Additionally, the ether which is used as a precipitant can be completely removed by evaporation and vacuum pump, whereby the precipitant can be completely removed and the concern of unknown side effects caused by chemical or bio-compatible additives in the fibrin glue may be eliminated. Finally, the fibrin glue with high tensile strength is produced by the techniques of this invention because the fibrin glue contains high concentrations of fibrinogen.

Although the present invention has been described in terms of the presently preferred embodiment, it is to be understood that such disclosure is not to be interpreted as limiting. Various alternatives and modifications will no doubt become apparent to those skilled in the art after reading the above disclosure. Accordingly, it is intended that the appended claims be interpreted as covering all alternatives and modifications as falling within the true spirit and scope of the invention.

We claim:

1. An apparatus for producing clinically ready fibrinogen of high concentration and high tensile strength from autologous plasma of a patient as part of a sterile and closed system, comprising:

receiving means for receiving a blood concentration from the patient;

a reservoir for providing a desirable amount of an anticoagulant to the blood concentration;

a plasma membrane separator to extract and separate the autologous plasma from other undesirable compositions in the blood concentration of the patient;

means for adding a desirable amount of ether or other suitable solvents containing an —OH group;

a second membrane separator to provide separation of fibrinogen from other compositions in the autologous plasma in the presence of said desirable amount of ether or other suitable solvents containing an —OH group wherein said second membrane separator further comprises a mixing means to provide thorough mixing of the autologous plasma with the ether or the suitable solvents containing an —OH group;

a fibrinogen collector connected to the second membrane separator to receive the fibrinogen separated and transferred from the second membrane separator;

a vacuum pump connected to the fibrinogen collector through a sterile filter to remove the ether or the other suitable solvents containing an —OH group contained within the fibrinogen collector;

a freezer enclosing said second membrane separator and said fibrinogen collector to provide adjustable temperatures to the autologous plasma in the second membrane separator and to the fibrinogen in the fibrinogen collector; and communication means for providing blood transferring among the receiving means, the reservoir, the plasma membrane separator, the second membrane separator and the fibrinogen collector wherein said communication means comprises at least one peristaltic pump to maintain blood transport in the sterile and closed system;

wherein by the use of said apparatus as part of a closed and sterile system, the concern of blood contamination due to exposure with air can be eliminated.

2. An apparatus for producing clinically ready fibrin glue of high concentration and high tensile strength from autologous plasma of a patient as part of a sterile and closed system, comprising:

receiving means for receiving a blood concentration from the patient;

a reservoir for providing a desirable amount of an anticoagulant to the blood concentration;

a plasma membrane separator to extract and separate the autologous plasma from other undesirable compositions in the blood concentration of the patient;

means for adding a desirable amount of ether or other suitable solvents containing an —OH group;

a second membrane separator to provide separation of fibrinogen from other compositions in the autologous plasma in the presence of said desirable amount of ether or other suitable solvents containing an —OH group wherein said second membrane separator further comprises a mixing means to provide thorough mixing of the autologous plasma with the ether or the suitable solvents containing an —OH group;

a fibrinogen collector connected to the second membrane separator to receive the fibrinogen separated and transferred from the second membrane separator;

a vacuum pump connected to the fibrinogen collector through a sterile filter to remove the ether or the other suitable solvents containing an —OH group contained within the fibrinogen collector;

a freezer enclosing said second membrane separator and said fibrinogen collector to provide adjustable temperatures to the autologous plasma in the second membrane separator and to the fibrinogen in the fibrinogen collector;

a mixer to mix the fibrinogen with an adequate concentration of thrombin and Ca++ to form the fibrin glue; and communication means for providing blood transferring among the receiving means, the reservoir, the plasma membrane separator, the second membrane separator and the fibrinogen collector wherein said communication means comprises at least one peristaltic pump to maintain blood transport in the sterile and closed system;

wherein by the use of said apparatus as part of a closed and sterile system, the concern of blood contamination due to exposure with air can be eliminated.

* * * * *